United States Patent
Wicke et al.

(10) Patent No.: US 6,900,471 B1
(45) Date of Patent: May 31, 2005

(54) METHOD FOR DEFINING THE COLOR GROUP OF AN LED AND LED MODULE

(75) Inventors: Markus Wicke, Lapperdorf (DE);
Christian Hacker, Regensburg (DE);
Burkard Wiesmann, Regensburg (DE);
Joachim Reill, Zeitlarn (DE)

(73) Assignee: Osram Opto Semiconductor GmbH, Regensburg (DE)

( * ) Notice: Subject to any disclaimer, the term of this patent is extended or adjusted under 35 U.S.C. 154(b) by 136 days.

(21) Appl. No.: 10/412,888

(22) Filed: Apr. 14, 2003

(30) Foreign Application Priority Data

Apr. 12, 2002 (DE) .......................................... 102 16 395

(51) Int. Cl.$^7$ .............................................. H01L 33/00
(52) U.S. Cl. ........................... 257/89; 356/402; 356/406
(58) Field of Search ................................ 356/402, 406; 257/89

(56) References Cited

U.S. PATENT DOCUMENTS 5,521,708 A * 5/1996 Beretta ........................ 356/402
5,770,917 A * 6/1998 Yano et al. .................. 313/486

OTHER PUBLICATIONS

K. Mahr et al., "Ein auf den Planckschen Strahler bezogenes Koordinatensystem für die Farbart", Technish-wissenschaftliche Abhandlungen der Orsram Gesellschaft (1969) vol. 10, p. 283–292.

International Commission on Illumination, "Method of Measuring and Specifying Colour Rendering Properties of Light Sources", Publication CIE No. 13.2, 1974 pp. 29–30.

Dr. Yoshi Ohno, "OSA Handbook of Optics, vol. III Visual Optics and Vision Chapter for Photometry and Radiometry" Oct. 20, 1999, pp. 10–13.

International Commission on Illumination, "COLORIMETRY", Second Edition, Publication CIE No. 15.2, 1986, pp. 38 and A1.

* cited by examiner

*Primary Examiner*—Long Pham
*Assistant Examiner*—Wai-Sing Louie
(74) *Attorney, Agent, or Firm*—Cohen, Pontani, Lieberman & Pavane

(57) ABSTRACT

Method for defining the color group of an LED which emits mixed-color, in particular white, light. The CIE color space is divided by means of a network with two sets of intersecting network lines, one set being provided by a set of Judd straight lines and the other set by the line for the color loci of a Planckian radiator and also the associated lines of constant threshold value deviation, so that the network has a plurality of network cells bounded by network lines. The color locus of the LED is determined, and the network cell is determined in which the color locus of the LED is located. The LED is assigned to the color group of the network cell.

9 Claims, 2 Drawing Sheets

METHOD FOR DEFINING THE COLOR GROUP OF AN LED AND LED MODULE

FIELD OF THE INVENTION

The invention relates to grouping LEDs such as in an LED module to achieve a color impression that is as homogenous as possible and, in particular, to white-light LEDs in which color fluctuations are particularly noticeable by the human eye.

BACKGROUND OF THE INVENTION

In LED modules with a plurality of white-light LEDs, use is usually made of LEDs which have been classified as of the same type with regard to their color and intensity during production. This serves the purpose of equipping a module with LEDs that are as far as possible identical, and of thereby achieving a color impression that is as homogeneous as possible.

However, during production, LEDs are generally sorted in relatively rudimentary fashion and divided into only a few groups. Moreover, this division is oriented toward production parameters. The color perception of the human eye is only of secondary importance in this case.

As a consequence, clearly visible fluctuations in the color impression may therefore occur in such LED modules. This problem is aggravated particularly in the case of white-light LEDs or white-light modules since deviations from the white point in the color space are particularly readily noticeable as a color cast.

SUMMARY OF THE INVENTION

One object of the present invention is to provide an improved method for defining the color group of an LED, in particular of a white-light LED.

Another object of the invention is to provide an arrangement of LEDs, for example an LED module, with the least possible deviation from a predetermined color locus.

These and other objects are attained in accordance with one aspect of the invention directed to a method for defining the color group of an LED which emits mixed-color, in particular white, light in accordance with a CIE color space. The CIE color space is divided by means of a grid network with two sets of intersecting network lines, one set being provided by a set of Judd straight lines and the other set by a line for the color loci of a Planckian radiator together with associated lines of constant threshold value deviation, so that the network includes a plurality of network cells bounded by network lines. The color locus of an LED is determined, and then the network cell is determined in which the color locus of the LED is located. The LED is assigned to the color group of the network cell.

Another aspect of the present invention is directed to an arrangement of a plurality of LEDs, wherein the LEDs have a color locus in the CIE color space, all the color loci being located in a region which is bounded by two Judd straight lines with a predetermined color temperature in each case and two lines with a predetermined, constant threshold value deviation in each case.

In a particular method according to the invention for defining the color group of an LED which emits mixed-color, in particular white, light, in a first step, the CIE color space is provided with a grid network. This network comprises two sets of intersecting network lines, one set being provided by a set of Judd straight lines and the other set by the line for the color loci of a Planckian radiator and also the associated lines of constant threshold value deviation, so that the network has a plurality of network cells bounded by network lines. In this case, each network cell is assigned a color group.

In the next step, the color locus of the LED is determined. Afterward, that network cell in which the color locus of the LED is located is ascertained. Finally, the LED is assigned to this network cell or the color group thereof.

As is well known, a CIE color space was defined by the Commission on Illumination (CIE) for use in illumination techniques. As is apparent from FIG. 2, essentially the CIE color space is the space of visible colors in an x-y coordinate system so that each color is represented by two coordinates. The "white point" is at the coordindates X=0.33 and y=0.33, and it defines "perfect" white.

Judd straight lines in the CIE color space are defined as straight lines of very similar color temperature. Judd lines are an approximation of so-called isotemperature lines which are defined to be normal to the line for the color loci of the Planckian radiator in a special representation of the CIE color space. See CIE, Colorimetry, 2nd ed., 1986, Chapter 5.5 and Appendix A3. (FIG. 1 is not to scale and, therefore, the Judd lines and the line for the color loci of the Planckian radiator are not perpendicular as shown therein). They may be regarded for purposes of an approximation, as lines of constant color temperature. The line for the color loci of a Planckian radiator is provided by the color loci of a Planckian radiator for different temperatures of the Planckian radiator. The distance between a color locus and said line is determined in threshold value units (TVU). In the context of the invention, lines which are composed of points of identical threshold value are referred to as lines of constant threshold value deviation.

A Planckian radiator is well known in optics and radiation physics since it represents the theoretical model for every body of a given color temperatre due to its thermal energy. The spectrum of a Planckian radiator can be found in any textbook on optics or thermodynamics, such as the OSA Handbook of Optics, Vol. III, Ch. 5.5.

The method according to the invention calculates the color locus of an LED on the basis of the human eye closely relying on the Planckian radiator and the Judd straight lines, that is to say straight lines of very similar color temperature. The LEDs are therefore sorted into groups which correspond to the color sense of perception of the human eye. The limits for this can be determined for example by means of tests with sample arrangements of LEDs. These limits of the sense of perception can then be used to orient and optimize the spacing of the grid network in the method according to the invention.

An LED module equipped with LEDs of the same color group, which has been determined by the method according to the invention, has advantageously low color deviations, in particular with regard to the color impression engendered.

In the case of adjacent network lines which are provided by lines of constant threshold value deviation, the difference in the assigned threshold value units is, by way of example, 20 threshold value units, preferably 10 threshold value units, particularly preferably 5 threshold value units.

In the case of adjacent network lines which correspond to Judd straight lines, the difference in the color temperature is, by way of example, 2000 K, preferably 1500 K, particularly preferably 1000 K.

In this case, it is expedient for the grid network to be spaced in non-uniform fashion, the size of the cells being chosen to be smaller in the vicinity of the white poinst, that is to say the color locus x=⅓, y=⅓, since the human eye is particularly sensitive to color deviations in this region.

In the case of an LED arrangement according to the invention, it is provided that the LEDs each have a color locus, which, in the CIE color space, all lie in a region which is bounded by two Judd straight lines with a predetermined color temperature in each case and two lines with a predetermined, constant threshold value deviation in each case. What is thus achieved, in accordance with the method described above, is that the LED arrangement exhibits advantageously small color deviations during operation.

Further features, advantages and expediencies of the invention emerge from the following description of an exemplary embodiment in conjunction with the figure.

DETAILED DESCRIPTION OF THE DRAWINGS

Figure 1:
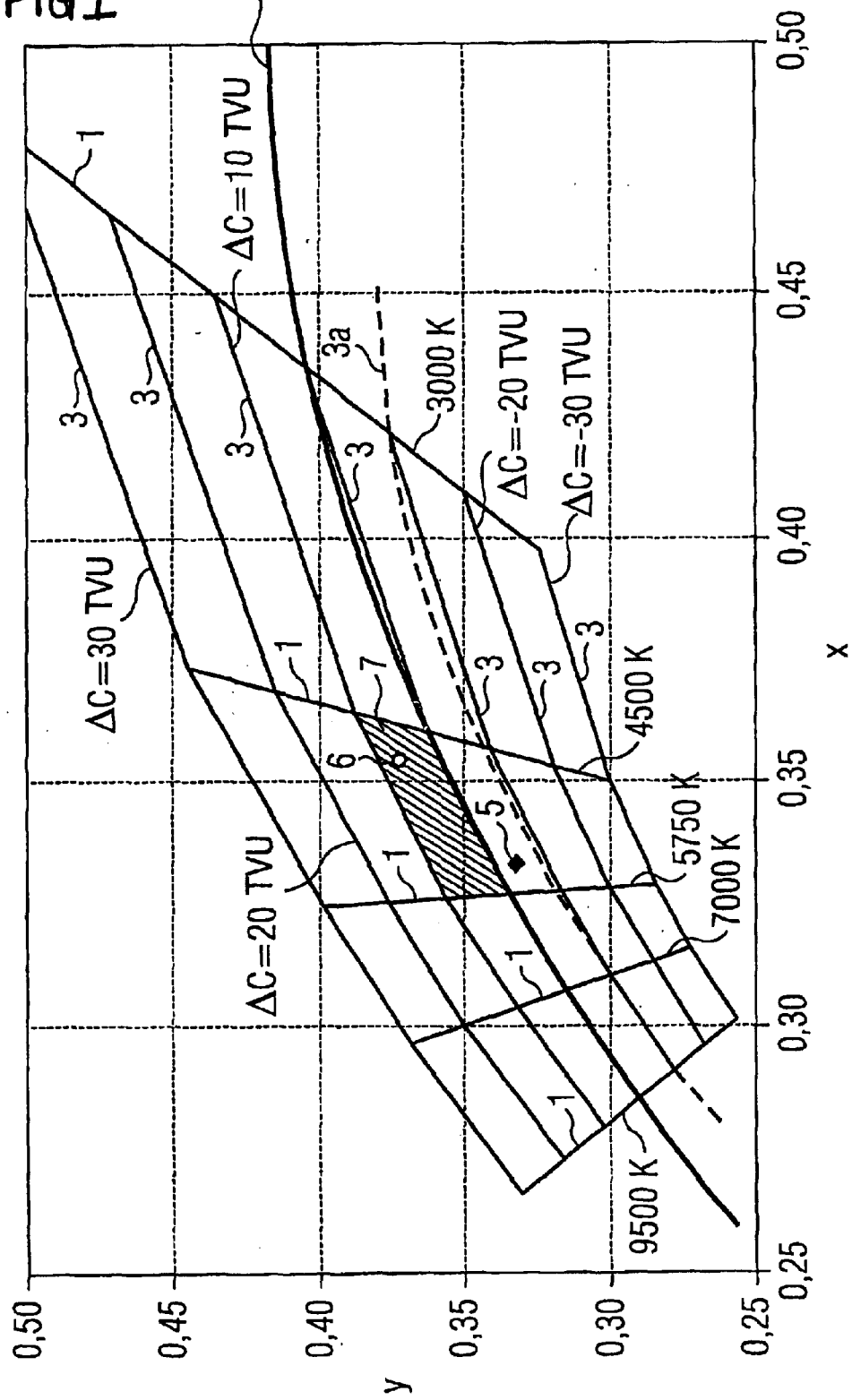
FIG. 1 shows a detail from the CIE color space in the vicinity of the white point 5, i.e. the color locus having the coordinates x=⅓, y=⅓.
Figure 2:
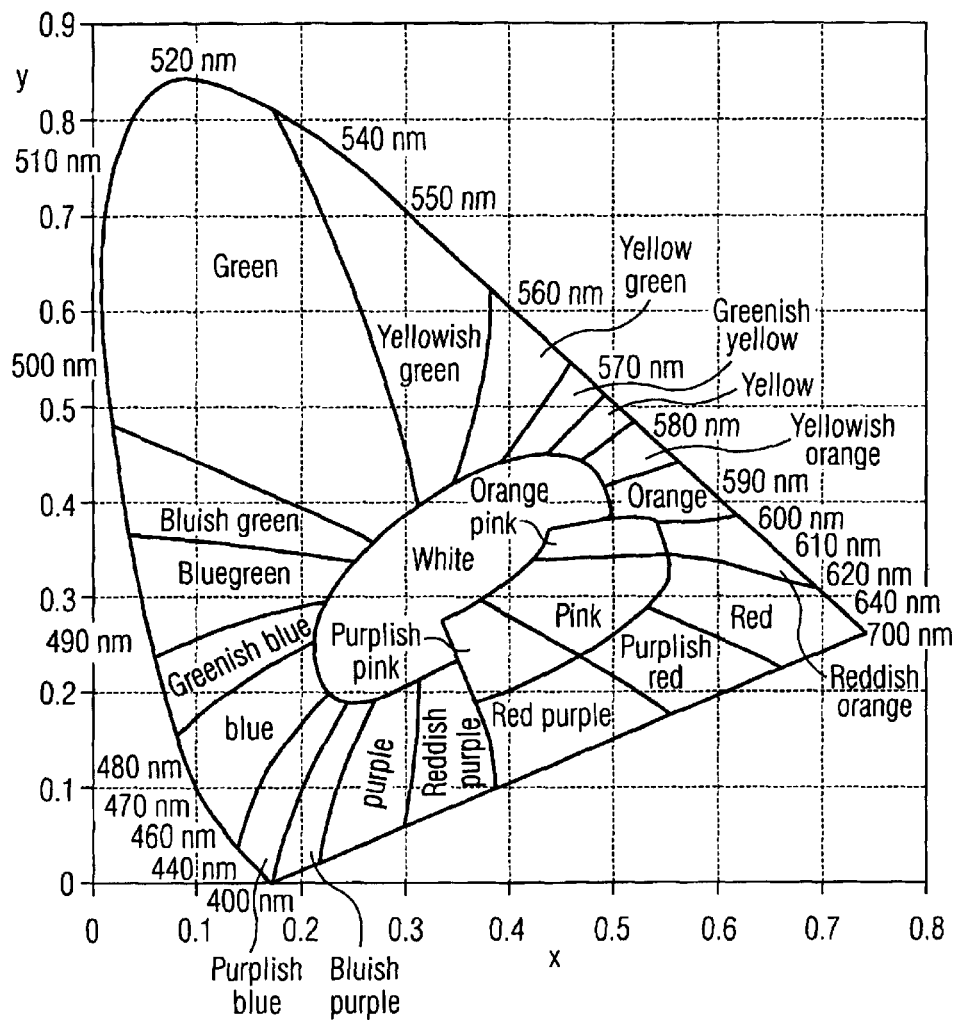
FIG. 2 shows the entire CIE color space, as is well known.

Five Judd straight lines 1 with the color temperatures 3000 K, 4500 K, 5750 K, 7000 K and 9000 K, which form a set of grid network lines, are entered in said figure in order to define the network for the method according to the invention. The line 2 of the color loci of a Planckian radiator and also a plurality of lines of constant threshold value deviation 3 are plotted as well. The difference with respect to the line 2 of the Planckian radiator 2 is specified in each case in threshold value units (TVU) and is −30 TVU, −20 TVU, −10 TVU, 10 TVU, 20 TVU and 30 TVU, respectively. TVUs are defined as the distance of two points in the CIE color space measured on the "scale" of the CIE color space and multiplied by 1000. Lines of constant threshold value deviation have a fixed distance from the line for the color loci of the Planckian radiator. The distance of a certain line of constant threshold value deviation from the line for the color loci of the Planckian radiator multiplied by 1000 yields the TVU of this certain line. The distance is defined in CIE, Method of Measuring and Specifying Colour Rendering Properties of Light Sources, 2nd ed., 4.3, formula (1), delta C.

The invention provides a classification for LEDs that is adapted to the color perception of the human eye. This means that LEDs of the same color group evoke the same color perception if the spacing of grid network lives is fine enough. This spacing can be determined empirically as follows. The color locus of each of a plurality of LEDs is marked in the CIE color space. Based on visual tests, a determination is made as to which of these LEDs cause the same color perception. From the result it is possible to derive the placement of grid lines in the CIE color space that group together LEDs which cause the same color perception and which separate those groups of LEDs from each other.

Thus, LEDs that seem to emit identical colors are grouped together and are separated from LEDs of different color by Judd straight lines and lines of constant threshold deviation, respectively.

The color locus of an LED can be determined by connecting the LED to a power supply, and the spectrum of the generated light is recorded electronically. The color locus is calculated from this spectrum in a well known manner.

For simplification, the lines of constant threshold value deviation 3 can be approximated here, as illustrated, by segment progressions. The latter are produced in that, proceeding from a line of constant threshold value deviation 3*a*, the points of intersection with the Judd straight lines are connected by straight-line sections. In the context of the invention, said segment progressions are also regarded as lines of constant threshold value deviation.

More widely, in the case of the invention, the Judd straight lines can also be replaced by lines having a constant x value, for example x=0.30, x=0.32, x=0.34, etc. Since the Judd straight lines run comparatively steeply with respect to the x axis, the resulting error can generally be tolerated.

In an exemplary embodiment of the invention, the following are determined in each case for the LEDs to be sorted: the color locus, illustrated by way of example by the point 6, and the associated network cell, illustrated in hatched fashion in the figure. All the LEDs which fall within the same network cell are then assigned to the same color group.

If LEDs divided into color groups according to a method of this type are used to form an LED arrangement, only LEDs of the same color group being used, then this arrangement has advantageously small color deviations.

The LEDs of such a module are characterized in that their color loci are located in a region which is bounded by two Judd straight lines with a predetermined color temperature in each case and two lines with a predetermined, constant threshold value deviation in each case.

It should be noted that white light in the context of the invention is not only purely white light with the color locus x=⅓, y=⅓, but also light which, deviating from this, is perceived as substantially white or whitish. In case of doubt, the definition of the color "white" used for the specification of vehicle lamps as set forth by the Economic Commission for Europe (ECE) can be consulted for this.

Although a preferred embodiment of the present invention has been described in detail above, variations and modifications thereto will be readily apparent to anyone with ordinary skill in the art. For example, the number of Judd lines and lines of constant threshold value deviation depends on the application of the LEDs and the precision needed for this application.

Thus, for some applications a classification like red/yellow/green is sufficient, whereas other applications may require a finer color scheme. In general, the number of lines depends on the largest deviation of the LED color from a given specification that is tolerated. For smaller deviations, more lines and a finer spaced grip network is needed.

The scope of protection of the invention is not limited to the examples given hereinabove. The invention is embodied in each novel characteristic and each combination of characteristics, which includes every combination of any features which are stated in the claims, even if this combination of features is not explicitly stated in the claims.

What is claimed is:

1. A method for defining the color group of an LED which emits mixed-color, in particular white, light in accordance with a CIE color space, comprising:

dividing the CIE color space by means of a network with two sets of intersecting network, lines, one set being provided by a set of Judd straight lines and the other set by a line for the color loci of a Planckian radiator together with associated lines of constant threshold value deviation, so that the network includes a plurality of network cells bounded by network lines, determining a color locus of an LED, determining the network cell in which the color locus of the LED is located, and assigning the LED to the color group of said network cell.

2. The method as claimed in claim 1, wherein, for adjacent network lines which are provided by lines of constant threshold value deviation, the difference between the assigned threshold values is less than or equal to 20 threshold value units.

3. The method as claimed in claim 2, wherein the difference between the assigned threshold values is less than or equal to 10 threshold value units.

4. The method as claimed in claim 3, wherein the difference between the assigned threshold values is less than or equal to 5 threshold value units.

5. The method as claimed in claim 1, wherein, for adjacent network lines which are provided by Judd straight lines, the Judd straight lines have color temperatures whose difference is less than or equal to 2000 K.

6. The method as claimed in claim 5, wherein the Judd straight lines have color temperatures whose difference is less than or equal to 1500 k.

7. The method as claimed in claim 6, wherein the Judd straight lines have color temperatures whose difference is less than or equal to 1000 k.

8. The method as claimed in claim 1, wherein the intersecting network lines are at least partly replaced between their points of intersection by straight line sections which connect the respective points of intersection.

9. The method as claimed in claim 1, wherein in a region containing the white point, the area of the network cells is smaller than outside said region.

* * * * *